(12) United States Patent
Feldman et al.

(10) Patent No.: US 9,532,718 B2
(45) Date of Patent: Jan. 3, 2017

(54) HEMOGLOBIN CONTRAST IN ULTRASOUND AND OPTICAL COHERENCE TOMOGRAPHY FOR DIAGNOSING DISEASED TISSUE, CANCERS, AND THE LIKE

(71) Applicant: BOARD OF REGENTS, THE UNIVERSITY OF TEXAS SYSTEM, Austin, TX (US)

(72) Inventors: Marc D. Feldman, Austin, TX (US); Thomas E. Milner, Austin, TX (US); Jung-Hwan Oh, Austin, TX (US)

(73) Assignee: Board of Regents, the University of Texas System, Austin, TX (US)

( * ) Notice: Subject to any disclaimer, the term of this patent is extended or adjusted under 35 U.S.C. 154(b) by 0 days.

(21) Appl. No.: 14/959,379

(22) Filed: Dec. 4, 2015

(65) Prior Publication Data

US 2016/0150962 A1 Jun. 2, 2016

Related U.S. Application Data

(60) Division of application No. 13/330,258, filed on Dec. 19, 2011, now Pat. No. 9,204,802, which is a continuation of application No. 11/620,562, filed on Jan. 5, 2007, now Pat. No. 8,162,834, which is a continuation-in-part of application No. 11/550,771, filed on Oct. 18, 2006, now Pat. No. 8,036,732.

(51) Int. Cl.
| | |
|---|---|
| *A61B 5/05* | (2006.01) |
| *A61B 5/00* | (2006.01) |
| *A61B 8/06* | (2006.01) |
| *A61B 5/145* | (2006.01) |

(52) U.S. Cl.
CPC .......... *A61B 5/0066* (2013.01); *A61B 5/0073* (2013.01); *A61B 5/14546* (2013.01); *A61B 8/06* (2013.01); *A61B 5/05* (2013.01)

(58) Field of Classification Search
CPC ....... A61B 5/0066; A61B 5/0073; A61B 5/05; A61B 5/14546; A61B 8/06
See application file for complete search history.

(56) References Cited

U.S. PATENT DOCUMENTS

| | | | |
|---|---|---|---|
| 5,109,276 A | 4/1992 | Nudelman et al. | 358/88 |
| 5,795,295 A | 8/1998 | Hellmuth et al. | 600/407 |
| 5,991,697 A | 11/1999 | Nelson et al. | 702/49 |
| 6,373,920 B1 | 4/2002 | Hsieh | 378/98.11 |
| 6,587,206 B1 | 7/2003 | Dogariu et al. | 356/479 |
| 6,608,684 B1 | 8/2003 | Gelikonov et al. | 356/479 |

(Continued)

FOREIGN PATENT DOCUMENTS

WO WO 2004/096049 11/2004 ............... A61B 6/00

OTHER PUBLICATIONS

Chen, Z., et al., "Optical Doppler tomographic imaging of fluid flow velocity in highly scattering media" *Optics Letters* 22(1): 64-66 (1997).

(Continued)

*Primary Examiner* — Mark Remaly
(74) *Attorney, Agent, or Firm* — J. Peter Paredes; David G. Rosenbaum; Rosenbaum IP, P.C.

(57) ABSTRACT

A novel contrast mechanism for diagnosing diseased tissue using Ultrasound, Doppler Ultrasonography, Optical Coherence Tomography, or optical Doppler tomography coupled with an externally applied temporally oscillating high-strength magnetic field.

14 Claims, 9 Drawing Sheets

(56) References Cited

U.S. PATENT DOCUMENTS

| | | |
|---|---|---|
| 6,687,010 B1 | 2/2004 | Horii et al. .................... 356/479 |
| 6,795,195 B1 | 9/2004 | Barbour et al. .............. 356/446 |
| 2001/0036002 A1 | 11/2001 | Tearney et al. ............... 359/287 |
| 2002/0049375 A1 | 4/2002 | Strommer et al. ............ 600/407 |
| 2002/0077546 A1 | 6/2002 | Aldefeld et al. ............. 600/424 |
| 2002/0190212 A1 | 12/2002 | Boas et al. ................. 250/341.1 |
| 2003/0023153 A1 | 1/2003 | Izatt et al. .................... 600/407 |
| 2003/0137669 A1 | 7/2003 | Rollins et al. ................ 356/479 |
| 2003/0220749 A1 | 11/2003 | Chen et al. ...................... 702/31 |
| 2003/0233033 A1 | 12/2003 | Korotko et al. ............. 600/301 |
| 2003/0236458 A1 | 12/2003 | Hochman ..................... 600/431 |
| 2004/0059220 A1 | 3/2004 | Mourad et al. ............... 600/442 |
| 2005/0018201 A1 | 1/2005 | de Boer et al. ............... 356/479 |
| 2005/0105788 A1 | 5/2005 | Turek et al. ..................... 382/31 |
| 2005/0113678 A1 | 5/2005 | Villard et al. ................ 600/425 |
| 2005/0168735 A1 | 8/2005 | Boppart et al. .............. 356/301 |
| 2005/0171433 A1 | 8/2005 | Boppart et al. .............. 600/473 |
| 2005/0190372 A1 | 9/2005 | Dogariu ........................ 356/479 |
| 2006/0058642 A1 | 3/2006 | Franconi et al. ............. 600/420 |
| 2006/0100528 A1 | 5/2006 | Chan et al. ................... 600/476 |
| 2006/0132790 A1 | 6/2006 | Gutin ............................ 356/479 |
| 2006/0142746 A1 | 6/2006 | Friedman et al. .............. 606/11 |
| 2007/0038121 A1 | 2/2007 | Feldman et al. .............. 600/476 |

OTHER PUBLICATIONS

Dave, D., et al., "Polarization-maintaining fiber-based optical low-coherence reflectometer for characterization and ranging of birefringence" *Optics Letters* 28(19): 1775-1777 (2003).

deBoer, J., et al., "Polarization-sensitive optical coherence tomography" *Handbook of Optical Coherence Tomography* pp. 237-274 (2002).

Kane, S., "Introduction to Physics in Modern Medicine" *Taylor & Francis/CRC Press*, Boca Raton, FL. p. 1 (2003).

Kemp, N., et al., "High-sensitivity determination of birefringence in turbid media with enhanced polarization-sensitive optical coherence tomography" *J Opt Soc Am A.* 22(3): 552-560 (2005).

Kim, J., et al., "Hemoglobin contrast in magnetomotive optical doppler tomography" *Optics Letters* 31(6): 778-780 (2006).

Lee, T.M., et al., "Engineered microsphere contrast agents for optical coherence tomography" *Optics Letters* 28(17): 1546-1548 (2003).

Loo, C., et al., "Nanoshell-enabled photonics-based imaging and therapy of cancer" *Technology in Cancer Research & Treatment* 3(1): 33-40 (2004).

Motta, M., et al., "High magnetic field effects on human deoxygenated hemoglobin light absorption" *Bioelectrochemistry and Bioenergetics* 47: 297-300 (1998).

Oldenburg, A., et al., "Imaging magnetically labeled cells with magnetomotive optical coherence tomography" *Optics Letters* 30(7): 747-749 (2005).

Otis, L.L., et al., "Quantifying labial blood flow using optical Doppler tomography" *Oral Surg Oral Med Oral Pathol Oral Radiol Endod* 98(2): 189-194 (2004).

Piao, D., et al., "Quantifying Doppler angle and mapping flow velocity by a combination of doppler-shift and doppler-bandwidth measurements in optical doppler tomography" *Applied Optics* 42(25): 5158-5166 (2003).

Raghunand, N., et al., "Microenvironmental and cellular consequences of altered blood flow in tumours" *The British Journal of Radiology* 76: S11-S22 (2003).

Rylander, C., et al., "Quantitative phase-contrast imaging of cells with phase-sensitive optical coherence microscopy" *Optics Letters* 29(13): 1509-1511 (2004).

Schenck, J.F., "Physical interactions of static magnetic fields with living tissues" *Progress in Biophysics and Molecular Biology* 87: 185-204 (2005).

Taylor, D.S. et al., "The magnetic susceptibility of the iron in ferrohemoglobin" *Journal of the American Chemical Society* 60: 1177-1181 (1938).

Wang, X.J., et al., "Characterization of fluid flow velocity by optical doppler tomography" *Optics Letters* 20(11): 1337-1339 (1995)—Abstract.

Yamamoto, T. et al., "A blood-oxygenation-dependent increase in blood viscosity due to a static magnetic field" *Phys Med Biol* 49: 3267-3277 (2004).

HEMOGLOBIN CONTRAST IN ULTRASOUND AND OPTICAL COHERENCE TOMOGRAPHY FOR DIAGNOSING DISEASED TISSUE, CANCERS, AND THE LIKE

CROSS-REFERENCE TO RELATED APPLICATIONS

The present application is a divisional from U.S. patent application Ser. No. 13/330,258, filed Dec. 19, 2011, which will issue as U.S. Pat. No. 9,204,802 on Dec. 8, 2015; which is a continuation from U.S. patent application Ser. No. 11/620,562, filed Jan. 5, 2007, which is now U.S. Pat. No. 8,162,834, issued Apr. 24, 2012; which is a continuation-in-part of U.S. patent application Ser. No. 11/550,771, filed Oct. 18, 2006, which is now U.S. Pat. No. 8,036,732, issued Oct. 11, 2011, all hereby incorporated by reference.

BACKGROUND

The present invention relates in general to the art of medical diagnostic imaging and in particular to imaging a blood flow or a blood supply using Ultrasound, Doppler Ultrasound, Optical Coherence Tomography (OCT), or Doppler OCT coupled with a temporally oscillating high-strength magnetic field to image diseased tissue.

One of the hallmark features of cancer is angiogenesis. Angiogenesis is the process by which new blood vessels grow from preexisting blood vessels. Angiogenesis is a fundamental step of tumors from a dormant state to a malignant state, with new blood vessels penetrating into cancerous growths and supplying nutrients and oxygen. Detection of such new blood vessel growth would be advantageous in detection and diagnosis of cancers and diseased tissue throughout the body. For example, angiogenesis is known to occur during coronary artery disease, peripheral artery disease, and stroke when there is insufficient blood supply. Therefore detection of angiogenesis and abnormal blood vessel formation would be advantageous in diagnosing diseased tissues such as cancer.

Also, the accurate determination of location and flow velocity of moving particles in highly scattering media, such as blood flow, is important for medical diagnostics. While the measurements of blood flow in the coronary arteries is an important aspect in diagnosing coronary artery diseases. Numerous non-invasive approaches have been developed using techniques such as Doppler ultrasound, conventional angiography, laser Doppler flowmetry and magnetic resonance angiography.

One common sensing technique involves the use of ultrasound. Using this technique, ultrasound is directed into the body of the patient and tiny particles such as red blood cells, which are suspended in the blood plasma, scatter the ultrasonic energy back towards the receiver or transducer. The transducer then converts the back-scattered ultrasonic energy into an electrical signal that is processed in some known manner to determine the presence of a flow and an estimate of the flow velocity.

Magnetic resonance imaging (MRI) is based on an imaging technique for magnetically exciting nuclear spins in a subject positioned in a static magnetic field by applying a radio-frequency (RF) signal of the Larmor frequency, and reconstructing an image using MR signals induced by the excitation. MRI is widely applied in clinical medicine because of its capability of clearly depicting the slightest tissue of human brain in vivo.

Magnetic resonance angiography (MRA) provides detailed angiographic images of the body in a non-invasive manner. In conventional MRA, which does not use contrast agents, magnetic resonance signal from flowing blood is optimized, while signal from stationary blood or tissue structures is suppressed. In contrast-enhanced MRA, a contrast agent is injected into the blood stream to achieve contrast between flowing blood and stationary tissue.

The commonly known echo planar imaging (EPI) is a rapid MRI technique, which is used to produce tomographic images at high acquisition rates, typically several images per second. Functional magnetic resonance imaging (fMRI) has been found useful in perfusion and/or diffusion studies and in dynamic-contrast studies, etc. However, images obtained in EPI experiments tend to be vulnerable to an artifact known as "ghosting" or "ghost images."

Optical coherence tomography (OCT) is a technology that allows for non-invasive, cross-sectional optical imaging of biological media with high spatial resolution and high sensitivity. OCT is an extension of low-coherence or white-light interferometry, in which a low temporal coherence light source is utilized to obtain precise localization of reflections internal to a probed structure along an optic axis. This technique is extended to enable scanning of the probe beam in the direction perpendicular to the optic axis, building up a two-dimensional reflectivity data set, used to create a cross-sectional gray-scale or false-color image of internal tissue backscatter.

OCT uses the short temporal coherence properties of broadband light to extract structural information from heterogeneous samples such as biologic tissue. OCT has been applied to imaging of biological tissue in vitro and in vivo. Systems and methods for substantially increasing the resolution of OCT and for increasing the information content of OCT images through coherent signal processing of the OCT interferogram data have been developed to provide cellular resolution (i.e., in the order of 5 micrometers). During the past decade, numerous advancements in OCT have been reported including real-time imaging speeds.

In diagnostic procedures utilizing OCT, it would also be desirable to monitor the flow of blood and/or other fluids, for example, to detect peripheral blood perfusion, to measure patency in small vessels, and to evaluate tissue necrosis. Another significant application would be in retinal perfusion analysis. Accordingly, it would be advantageous to combine Doppler flow monitoring with the above micron-scale resolution OCT imaging in tissue.

Conventional OCT imaging primarily utilizes a single backscattering feature to display intensity images. Functional OCT techniques process the backscattered light to provide additional information on birefringence, and flow properties. (See for example, Kemp N J, Park J, Zaatar H N, Rylander H G, Milner T E, High-sensitivity determination of birefringence in turbid media with enhanced polarization-sensitive optical coherence tomography, Journal of the Optical Society of America A: Optics Image Science and Vision 2005, 22(3):552-560; Dave D P, Akkin T, Milner T E, Polarization-maintaining fiber-based optical low-coherence reflectometer for characterization and ranging of birefringence, Optics Letters 2003, 28(19):1775-1777; Rylander C G, Dave D P, Akkin T, Milner T E, Diller K R, Welch M, Quantitative phase-contrast imaging of cells with phase-sensitive optical coherence microscopy, Optics Letters 2004, 29(13):1509-1511; de Boer J F, Milner T E, Ducros M G, Srinivas S M, Nelson J S, Polarization-sensitive optical coherence tomography, Handbook of Optical Coherence Tomography, New York: Marcel Dekker, Inc., 2002, pp 237-274.)

Since the ability to characterize fluid flow velocity using OCT was demonstrated by Wang et al., several phase resolved, real-time optical Doppler tomography (ODT) approaches have been reported. (See for example, Chen Z P, Milner T E, Dave D, Nelson J S, Optical Doppler tomographic imaging of fluid flow velocity in highly scattering media, Optics Letters 1997, 22(1):64-66; Wang X J, Milner T E, Nelson J S.

Optical Doppler tomography (ODT) combines Doppler velocimetry with optical coherence tomography (OCT) for noninvasive location and measurement of particle flow velocity in highly scattering media with micrometer-scale spatial resolution. The principle employed in ODT is very similar to that used in radar, sonar and medical ultrasound. ODT uses a low coherence or broadband light source and optical interferometer to obtain high spatial resolution gating with a high speed scanning device such as a conventional rapid scanning optical delay line (RSOD) to perform fast ranging of microstructure and particle motion detection in biological tissues or other turbid media.

To detect the Doppler frequency shift signal induced by the moving particles, several algorithms and hardware schemes have been developed for ODT. The most straight-forward method to determine the frequency shift involves the use of a short time fast Fourier transform (STFFT). However, the sensitivity of this method is mainly dependent on the FFT time window, which limits axial scanning speed and spatial resolution when measuring slowly moving blood flow in small vessels that requires high velocity sensitivity. However, a phase-resolved technique can decouple the Doppler sensitivity and spatial resolution while maintaining high axial scanning speed.

In ODT, the Doppler frequency shift is proportional to the cosine of the angle between the probe beam and the scatterer's flow direction. When the two directions are perpendicular, the Doppler shift is zero. Because a priori knowledge of the Doppler angle is not available, and conventional intensity OCT imaging provides a low contrast image of microvasculature structure, detecting small vessels with slow flow rates is difficult. However, the Doppler angle can be estimated by combining Doppler shift and Doppler bandwidth measurements. (See for example, Piao D Q, Zhu Q, Quantifying Doppler Angle and Mapping Flow Velocity by a Combination of Doppler-shift and Doppler-bandwidth Measurements in Optical Doppler Tomography, *Applied Optics,* 2003, 42(25): 5158-5166, and U.S. Pat. No. 5,991, 697 describe a method and apparatus for Optical Doppler Tomographic imaging of a fluid flow in a highly scattering medium comprising the steps of scanning a fluid flow sample with an optical source of at least partially coherent radiation through an interferometer, which is incorporated herein by reference).

The ability to locate precisely the microvasculature is important for diagnostics and treatments requiring characterization of blood flow. Recently, several efforts to increase blood flow contrast mechanisms have been reported including protein microspheres incorporating nanoparticles into their shells, plasmon-resonant gold nanoshells, and use of magnetically susceptible micrometer sized particles with an externally applied magnetic field. (See for example, Lee T M, Oldenburg A L, Sitafalwalla S, Marks D L, Luo W, Toublan F J J, Suslick K S, Boppart S A, Engineered microsphere contrast agents for optical coherence tomography, *Optics Letters,* 2003, 28(17): 1546-1548; Loo C, Lin A, Hirsch L, Lee M H, Barton J, Halas N, West J, Drezek R. Nanoshell-enabled photonics-based imaging and therapy of cancer. *Technology in Cancer Research & Treatment,* 2004; 3(1): 33-40; and Oldenburg A L, Gunther J R, Boppart S A, Imaging magnetically labeled cells with magnetomotive optical coherence tomography, *Optics Letters,* 2005, 30(7): 747-749.)

Wang, et al., "Characterization of Fluid Flow Velocity by Optical Doppler Tomography," *Optics Letters,* Vol. 20, No. 11, Jun. 1, 1995, describes an Optical Doppler Tomography system and method which uses optical low coherence reflectrometry in combination with the Doppler effect to measure axial profiles of fluid flow velocity in a sample. A disadvantage of the Wang system is that it does not provide a method to determine direction of flow within the sample and also does not provide a method for generating a two-dimensional color image of the sample indicating the flow velocity and directions within the image.

The use of an externally applied field to move magnetically susceptible particles in tissue has been termed magneto-motive OCT (MM-OCT). Functional magnetic resonance imaging (fMRI) detects deoxyhemoglobin which is a paramagnetic molecule. However, the paramagnetic susceptibility of human tissue is very low compared to other biocompatible agents such as ferumoxides (nanometer sized iron oxide particles). Therefore, it was believed that, other than differentiating relaxation times (T2) between oxygenated and deoxygenated blood, the magnetic field strength required to produce a retarding force on blood flow was well above that of current imaging fields. (See also, for example, Schenck J F., Physical interactions of static magnetic fields with living tissues, Progress in Biophysics and Molecular Biology 2005, 87 (2-3):185-204; and Taylor D S, Coryell, C. D., Magnetic susceptibility of iron in hemoglobin. J. Am. Chem. Soc. 1938, 60:1177-1181.)

The embodiments disclosed herein is a novel extension of ultrasound, Doppler ultrasound, OCT, or Doppler OCT to image hemoglobin in blood erythrocytes connected with diseased tissue.

SUMMARY OF THE INVENTION

A method and apparatus of imaging a blood flow or a blood supply using ultrasound in order to diagnosis a diseased tissue comprises an oscillating high-strength magnetic field with an ultrasound system to detect hemoglobin moving according to the magnetic field gradient.

Another embodiment is a method and apparatus of imaging a blood flow using optical coherence tomography in order to diagnosis a diseased tissue comprises an externally applied oscillating magnetic field with an optical coherence tomography system to detect hemoglobin moving according to the magnetic field gradient.

Another embodiment is a system for diagnosing diseased tissue comprising a magnetic field generator for applying an oscillating magnetic field to the tissue, and an ultrasound detection system for detecting a blood flow while it is in the presence of the oscillating magnetic field.

BRIEF DESCRIPTION OF THE DRAWINGS

FIGS. 3a and 3b are OCT and ODT images of a stationary turbid solution without an external magnetic field, respectively.

FIGS. 4a-4d are M-mode ODT images of the diluted deoxygenated blood flow (18% hematocrit) without and with an external magnetic field. FIG. 4a and FIG. 4b are ODT images of 5 mm/s blood flow without and with a 5 Hz magnetic field, respectively.

DETAILED DESCRIPTION OF THE INVENTION

Magneto-Motive Optical Doppler Tomography (MM-ODT) for improved Doppler imaging of blood flow or blood supply using an oscillating magnetic field is described below. By introducing mechanical movement of red blood cells (RBC's) during blood flow by a temporally oscillating high-strength magnetic field, MM-ODT allows imaging of blood flow, velocity, and blood supply. The controlled and increased Doppler frequency in MM-ODT provides an investigational tool to study in vivo blood transport, as shown in the article Hemoglobin Contrast in Magnetomotive Optical Doppler Tomography, Opt. Lett. 31, 778-780 (2006), herein incorporated by reference. Imaging blood flow or blood supply includes blood anywhere throughout the circulatory system or the body.

The microstructure of the blood flow and flow velocity information are all encoded in the interferogram of a Doppler OCT system. It should be readily apparent to those skilled in the optical arts, that different OCT systems and different OCT information can be used to determine the Doppler frequency shift. It is not intended to suggest any limitation as to the scope or functionality with different OCT architectures or optical information used with an oscillating magnetic field, such as time domain Doppler OCT and spectral domain Doppler OCT. Time domain OCT requires a mirror in the reference arm scanning at a constant velocity, while spectral domain OCT includes swept source OCT and Fourier domain OCT. An example of time-domain Doppler OCT is provided below.

Figure 1:
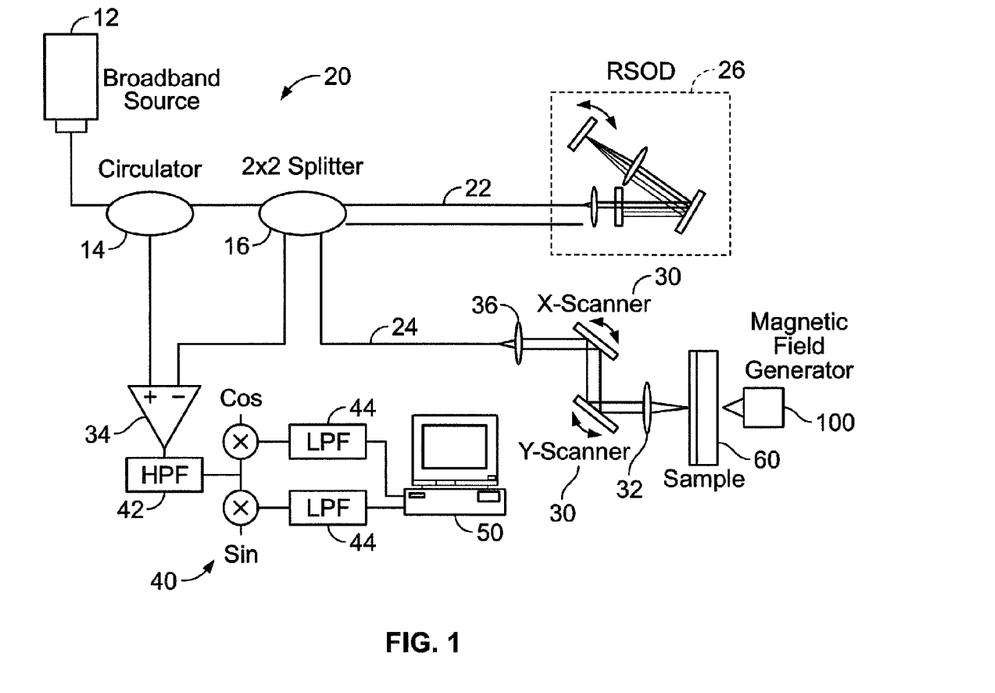
FIG. 1 is a schematic diagram of the MM-ODT system.

A schematic of the MM-ODT apparatus 10 is shown in FIG. 1. The OCT light source 12 comprises a super luminescent diode, which is used as the low coherence light source. In one embodiment, light source 12 is centered at 1.3 µm with a bandwidth of 90 nm. Light from source 12 is coupled into a single-mode optical fiber based interferometer 20 by circulator 14, where the interferometer 20 can provide 1 mW of optical power at the sample 60. Light is split into a reference arm 22 and sample arm 24 by a 2×2 splitter 16. A rapid-scanning optical delay (RSOD) line 26 is coupled to the reference arm 22. In one embodiment, the rapid-scanning optical delay line 26 is aligned such that no phase modulation is generated when the group phase delay is scanned at ~4 kHz. In the sample arm 24, a collimated beam 36 is redirected to sample 60 by two galvanometers 30 that permit three-dimensional scanning. In one embodiment, the galvanometers can be an X-scanner and a Y-scanner. The sample 60 can be internal or external to the body, where the probe beam is focused by an objective lens 32. In one embodiment, the objective lens 32 yields a 10-µm spot at the focal point. Phase modulation can be generated using an electro-optical waveguide phase modulator, which can produce a carrier frequency (~1 MHz). And the magnetic field generator 100 is in proximity to the sample 60.

A dual-balanced photodetector 34 is coupled to the 2×2 splitter 16 and the circulator 14. The photodetector 34 of a 80 MHz bandwidth reduces the light source noise from the OCT interference signal. A hardware in-phase and quadrature demodulator 40 with high/bandpass filters 42 and low/bandpass filters 44 improves imaging speed. Doppler information was calculated with the Kasai autocorrelation velocity estimator. Labview software 50 (National Instruments, Austin, Tex.) is coupled to the MM-ODT system with a dual processor based multitasking scheme. The maximum frame rate of the MM-ODT system 10 was 16 frames per second for a 400×512 pixel sized image. The Doppler frequency shift can be determined with the use of a short time fast Fourier transform (STFFT). Alternatively, a phase-resolved technique can determine the Doppler frequency shift to decouple the Doppler sensitivity and spatial resolution while maintaining high axial scanning speed. Alternatively, differential phase optical coherence tomography (OCT) or spectral domain phase-sensitive OCT can be used to determine the Doppler frequency shift, as readily determined by one skilled in the optical arts.

Figure 2:
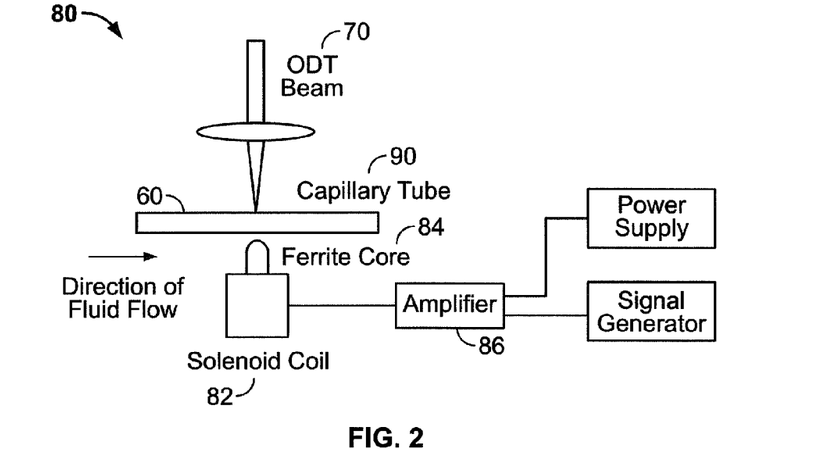
FIG. 2 is a schematic diagram of the probe beam, flow sample and solenoid coil.
Figure 3A:
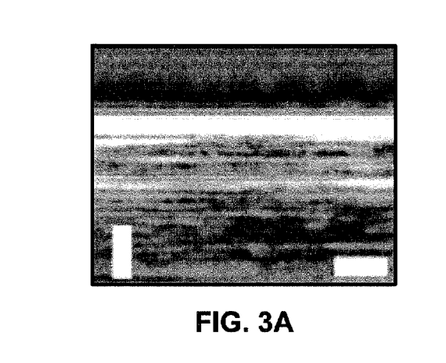
Figure 3B:
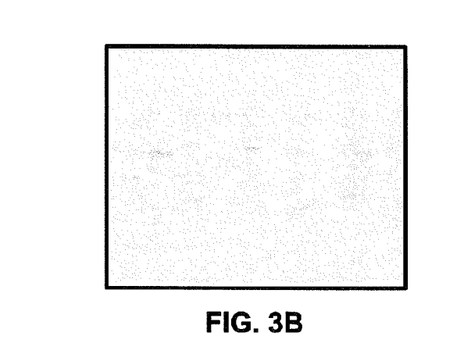
Figure 3C:
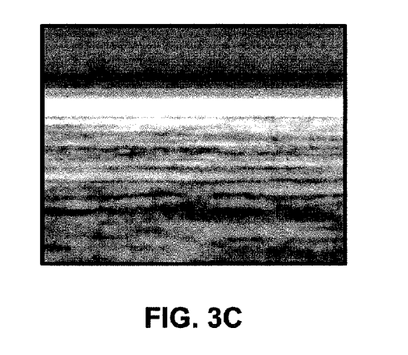
FIG. 3c and FIG. 3d are OCT and ODT images with a 50 Hz magnetic field, respectively. The white bar represents 200 µm, accordingly.
Figure 3D:
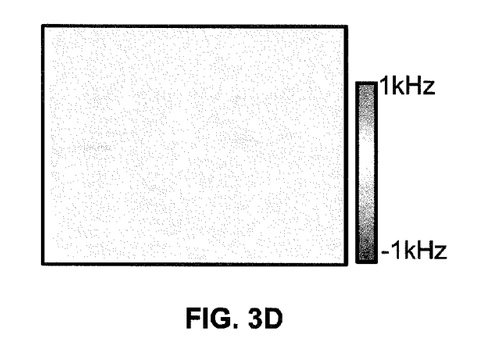

FIG. 2 shows an example of the magnetic field generator 80 with a capillary tube 90. The magnetic field generator 80 includes a solenoid coil 82 (Ledex 4EF) with a cone-shaped ferrite core 84 at the center and driven by a current amplifier 86 supplying up to 960 W of power. The magnetic field generator 80 can be placed underneath the sample 60 during MM-ODT imaging. The combination of the ferrite core 84 and solenoid coil 82 using a high power operation dramatically increases the magnetic field strength ($B_{max}$=0.14 Tesla) at the tip of the core 82 and also focuses the magnetic force on the targeted samples 60. The sinusoidal current can vary the magnetic force applied to the capillary tube 90 in order to introduce movement of magnetic fluids, which include red blood cells that contain hemoglobin. In one embodiment, the probe beam is oriented parallel to the gradient of the magnetic field's strength.

The material parameter characterizing magnetic materials, including biological tissue, is the magnetic volume susceptibility, $\chi$. Magnetic volume susceptibility is dimensionless in SI units and is defined by the equation $M=\chi H$, where M is the magnetization at the point in question and H is the local density of the magnetic field strength. Hemoglobin's high iron content, due to four Fe atoms in each hemoglobin molecule, and the large concentration of hemoglobin in human red blood cells give Hemoglobin magnetomotive effects in biological tissue. The magnetic volume susceptibility of the hemoglobin molecule consists of a paramagnetic component due to the electron spins of the four iron atoms. The paramagnetic susceptibility is given by the Curie Law, $$\chi = \frac{\mu_o N_p (\mu_{eff}^2 \mu_B^2)}{3kT} \quad (1)$$

where $\mu_o$ is permeability of free space and has the value $4\pi \times 10^7$ H/m, $N_p$ is the volume density of paramagnetic iron atoms in hemoglobin, $N_p = 4.97 \times 10^{25}$ iron atoms/m³, $\mu_{eff}$ is the effective number of Bohr magnetons per atom reported as 5.35, and the Bohr magneton, $\mu_B = 9.274 \times 10^{-24}$ J/T, and Boltzmann's constant, $k = 1.38 \times 10^{-23}$ J/K, and T is the absolute temperature (K). The calculated susceptibility of a RBC is about $11 \times 10^{-6}$ assuming a 90% concentration of hemoglobin per RBC. The calculated susceptibility of a RBC is dependent on the oxygenation of the hemoglobin. The calculations can be adjusted accordingly, depending on the oxygenation of the RBC, which can be measured by known techniques.

A RBC placed in a magnetic field gradient experiences forces and torques that tend to position and align it with respect to the field's direction. The magnetic force, in the direction of the probing light z, is given by $$F_z = m_{RBC} \frac{\delta^2 z(t)}{dt^2} = \frac{\delta U}{\delta z} = \frac{\chi V}{\mu_o} B \frac{\delta B}{\delta z}, \quad (2)$$

where V is the particle volume, B is the magnitude of the magnetic flux density, and $\Delta \chi$ is the difference between the susceptibility of the particle and the surrounding medium. The displacement [z(t)] of an RBC driven by a time varying magnetic flux density can be included in the analytic OCT fringe expression, $I_f$, $$I_f a 2 \sqrt{I_r I_s \exp\left[i\left(2\pi f_o t + \frac{4\pi z(t)}{\lambda_o} z(t)\right)\right]}, \quad (3)$$

where $I_R$ and $I_S$ are the back scattered intensities from the reference and sample arms, respectively, $f_o$ is the fringe carrier frequency, $\lambda_o$ is the center wavelength of the light source, and z(t) is the RBC displacement. Integration of all forces (magnetic, elastic, and viscous) on the RBC gives displacement, $z(t) = A \cos(4\pi f_m t)$ where A is a constant in units of length and $f_m$ is the modulation frequency of the magnetic flux density. In free space, the displacement, z(t), is dominated a constant acceleration which can be, however, ignored in confined models (i.e. blood vessel or capillary tube) with assumptions that, first, the probing area is much smaller than magnetic field area, and that secondly probing time starts after steady states of inner pressures. Expansion of the right-hand side of Eq. (3) using Bessel functions gives $$I_f a 2 \sqrt{I_R I_S} \quad (4)$$

$$\left(\sum_{k=0}^{\infty} (J_k(m) \exp(ik 4\pi f_m t)) + \sum_{k=0}^{\infty} ((-1)^k J_k(m) \exp(-ik 4 p f_m t))\right)$$

$$\exp(i 2\pi f_o t)$$

where $J_k(m)$ is the Bessel function of the first kind of order k for argument m which is $4\pi A/\lambda_o$. The amplitude of the $k^{th}$ sideband is proportional to $J_{k(m)}$. In coherent detection, the fraction of optical power transferred into each of the first order sidebands is $(J_1(m))^2$, and the fraction of optical power that remains in the carrier is $(J_o(m))^2$.

Example 1

MM-ODT Imaging of the Doppler Shift of Hemoglobin by Applying an Oscillating Magnetic Field to a Moving Blood Sample M-mode OCT/ODT images of a capillary glass tube filled with a stationary turbid solution with and without an external magnetic field as a control sample were recorded, as shown in FIGS. 3-4. A 750 µm-inner diameter glass capillary tube 200 was placed perpendicularly to the probing beam 70, as shown in FIG. 2. Fluids used for flow studies were injected through the tube at a constant flow rate controlled by a dual-syringe pump (Harvard Apparatus 11 Plus, Holliston, Mass.) with ±0.5% flow rate accuracy. The turbid solution was a mixture of deionized water and 0.5-gm latex microspheres ($\mu_s = 5$ mm$^{-1}$). The magnetic flux density and its frequency were approximately 0.14 T and 50 Hz, respectively. M-mode OCT/ODT images were acquired for 100 ms per frame. FIGS. 3a and 3b show M-mode OCT and ODT images without any external magnetic field, respectively. The ODT image in FIG. 3b contains small random phase fluctuations due to ambient vibration through the optical path. FIGS. 3c and 3d show M-mode OCT and ODT images with a 50 Hz external magnetic field, respectively. No distinguishable Doppler shift could be observed in the ODT image FIG. 3d indicating no interaction between the external magnetic field and the moving microspheres.

Deoxygenated blood was extracted from the vein of a human male's left arm, and diluted with saline. During preparation, blood was not exposed directly to air so as to remain deoxygenated. To simulate flow, blood was injected through the capillary tube 200 by a syringe pump at a relatively constant flow rate. As FIG. 4 shows, the oscillating Doppler frequency shift, resulting from RBC movement, could be observed at two different flow rates (5 and 30 mm/s). Because the flow direction was nearly perpendicular to the probing beam no significant Doppler frequency shift was distinguishable at the 5 mm/s flow rate FIG. 4a without any external magnetic field. In the case of the high blood flow rate of 30 mm/s, as shown at FIG. 4c, the Doppler frequency shift caused by the blood flow could be observed. And for maximum contrast enhancement, the probe beam can be directed parallel to the gradient of the magnetic field's strength. However, application of a 50 Hz magnetic field increased the Doppler contrast of blood at both the slow and fast flow rates as shown at FIGS. 4b and 4d. The high flow rate of 30 mm/s gives a higher contrast image than the low flow rate image, but the Doppler frequency shift of the former as a function of depth is less homogeneous than the latter, which is indicative of perturbation by blood flow. The same blood was diluted to 5 hematocrit (HCT), but no RBC movement could be observed below 8% HCT.

Figure 4A:
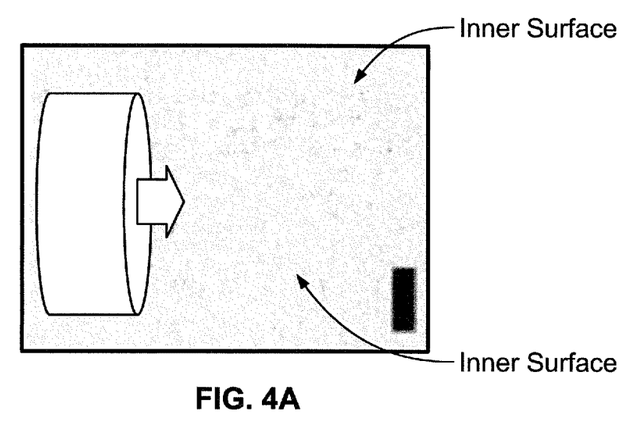
Figure 4B:
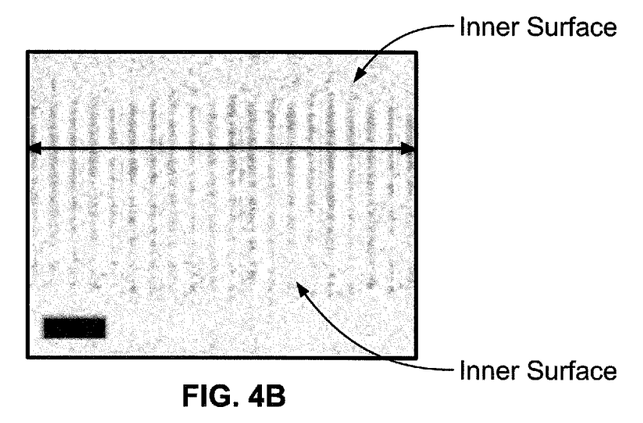
Figure 4C:
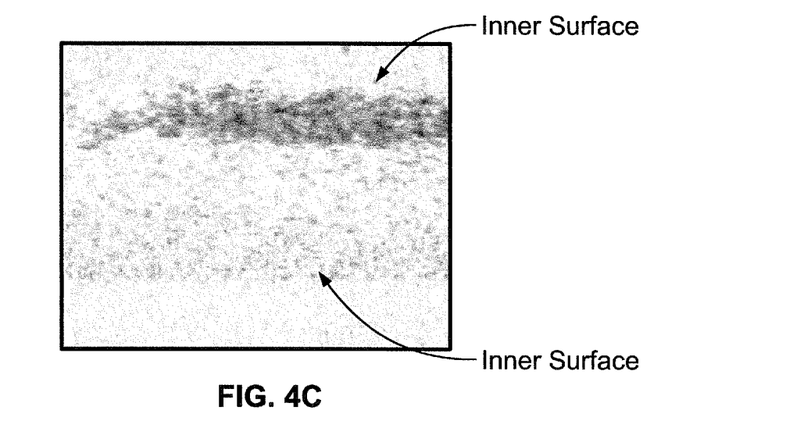
FIG. 4c and FIG. 4d are ODT images of 30 mm/s blood flow without and with a 50 Hz magnetic field, respectively. The Black bar indicates 200 µm, accordingly.
Figure 4D:
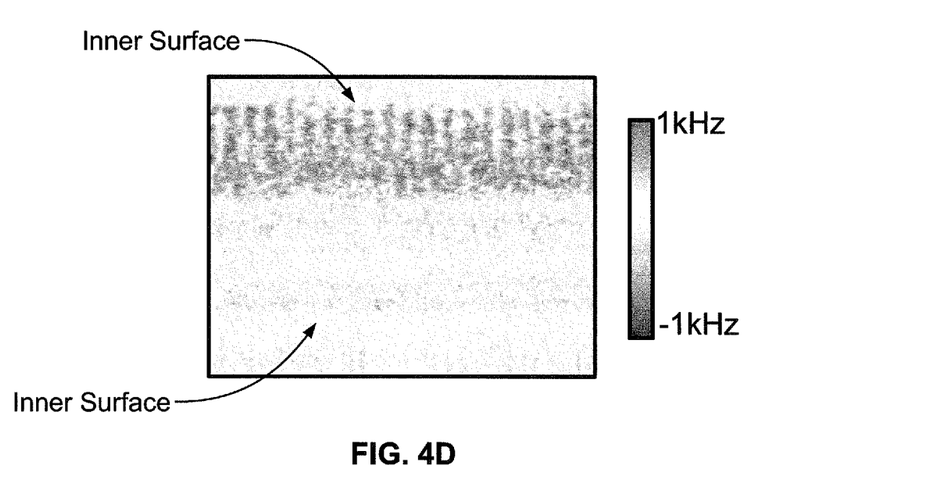
Figure 5A:
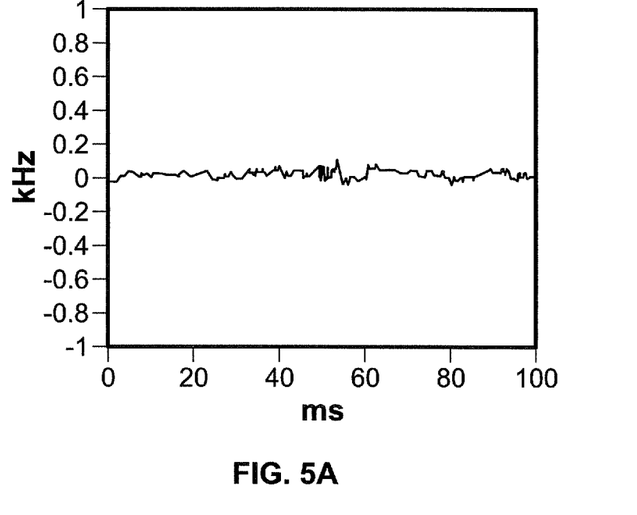
FIG. 5a and FIG. 5b are the Doppler frequency shift profiles without an external magnetic field, and with a 50 Hz magnetic field, respectively.

Doppler frequency shift profiles were calculated from the ODT images by averaging 20 lines at a selected depth indicated by horizontal arrows, as shown in FIGS. 4a and 4b. FIG. 5a indicates no significant Doppler frequency shift over a 100 ms time period, whereas FIG. 5b displays ±200 to 300 Hz Doppler frequency shifts oscillating 20 times over 100 ms (200 Hz).

Figure 5B:
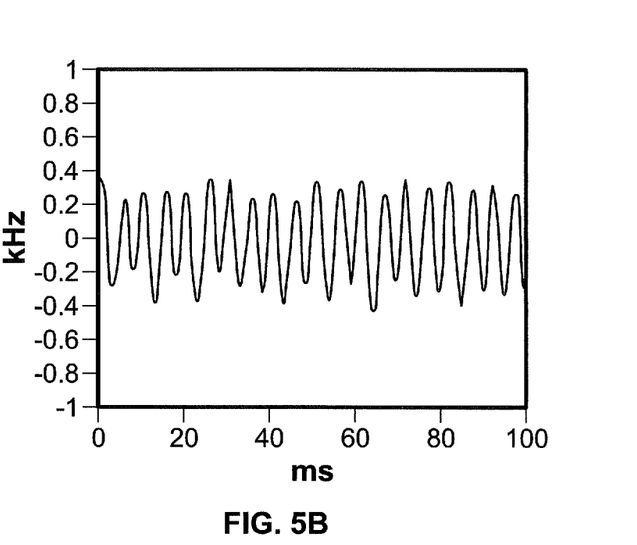

The Doppler frequency shift indicates that RBC's physically move into and away from the incident light while passing through the external magnetic field depending on whether their magnetic properties are paramagnetic or diamagnetic, as shown in FIG. 4, and that the 200 Hz oscillation of the Doppler frequency shift correlates with the 50 Hz magnetic field, as shown in FIG. 5. Frequencies 4 times higher than that of the external magnetic field ($f_m$) can be observed. According to Eq. 2, the frequency of the force on paramagnetic targets was twice that of the magnetic flux density; therefore, a 50 Hz B field displaces the targets at 100 Hz. Although the fringe signal (Eq. 4) contains harmonics at frequency ($2f_m$), the modulation frequency, $f_m$, was set so that the second-order sideband ($4f_m$) was dominant as shown in FIG. 5b. The particle motion can not be described as a pure sinusoidal function even if the modulated magnetic field is sinusoidal, due to the numerous forces that contribute to the motion within the field such as gravity, concentration gradient, and colloidal dispersion.

The new investigational tool may study in vivo blood transport and is the first implementation of MM-ODT for improved Doppler imaging of blood flow using an external oscillating magnetic field introducing a mechanical movement of RBC's during blood flow by a temporally oscillating high-strength magnetic field. MM-ODT to allow imaging of tissue function in a manner similar to functional magnetic resonance images (f-MRI) of deoxygenated blood in organs, when the sample arm of the MM-ODT system is coupled to a probe (not shown). Such probes are generally known in the arts, such as endoscopic probes, catheter probes, and the like.

Alternatively, the MM-ODT can be used for Port-Wine vessel mapping and Skin Cancer vessel mapping. The MM-ODT can be used to detect blood vessel location and size for cancer and port-wine stains, since these conditions are characterized by blood vessel growth and increases in hemoglobin content. Accordingly, other blood vessel detection for tissue abnormality identification can be envisioned with the embodiments disclosed herein. Generally, the MM-ODT can be used wherever blood flow detection is necessary in operations, chemotherapy, hemodialysis, and the like.

Figure 6:
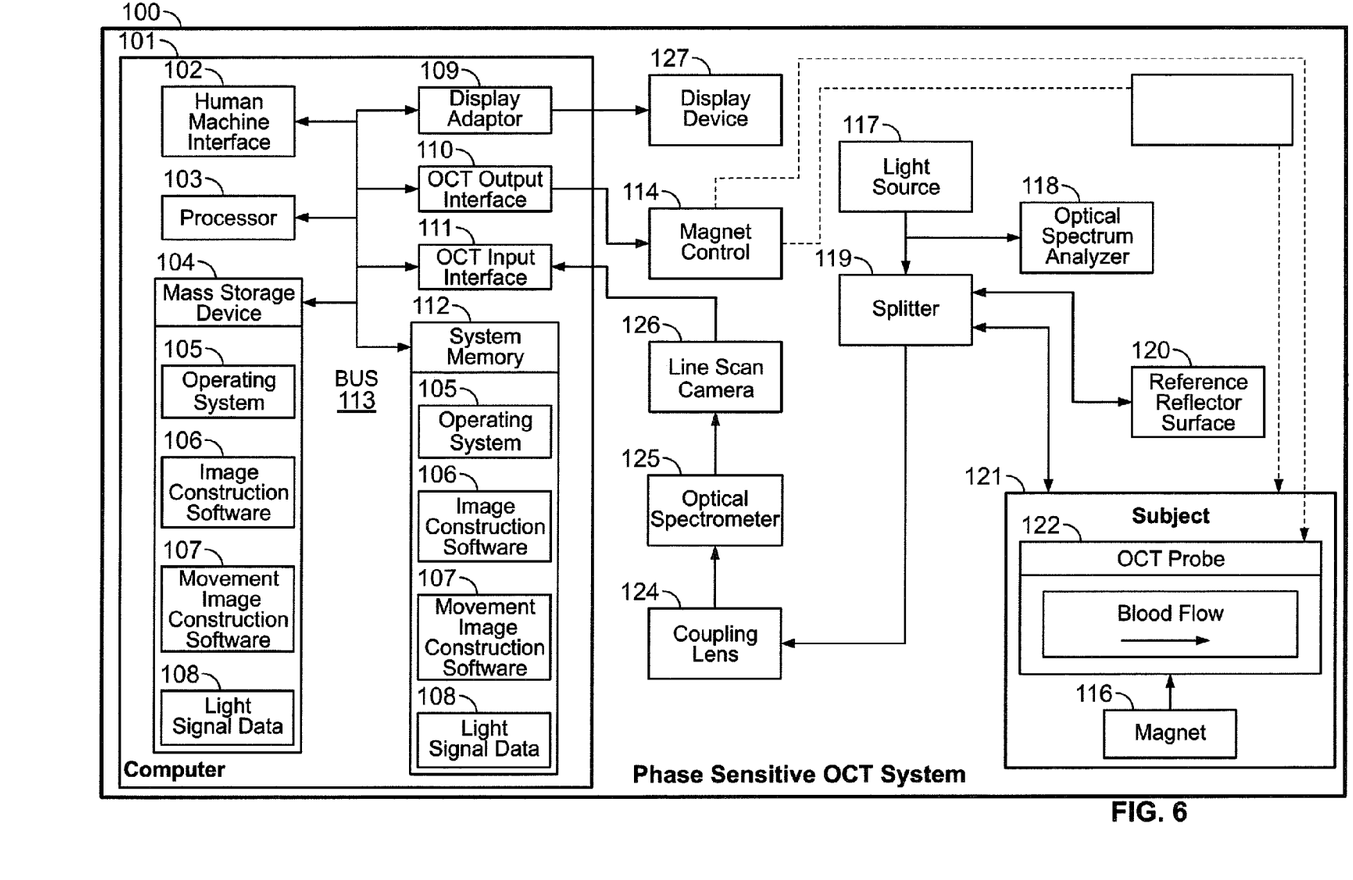
FIG. 6 is a block diagram illustrating an exemplary phase sensitive OCT system.

A spectral domain phase sensitive OCT system 100 can be used to image the blood flow and determine velocity information, when an oscillating magnetic field is applied to the blood flow, as shown in FIG. 6. Spectral domain phase sensitive OCT generally uses a broadband light source in a general interferometric setup, where the mirror in the reference typically does not move or does not require a rapid scanning delay line. A spectral interferogram is detected, in which each A-scan is entirely encoded. A Fourier transformation of the A-scan and velocity distribution of the blood flow can be extracted by known methods. In spectral domain Doppler OCT, the blood flow profile is the envelope of a calculated A-scan through Fourier transformation on the spectral interferogram. Velocity information is encoded in the phase of the interferogram. The Doppler velocity can be extracted by measuring the phase shift between two successive calculated A-scans in spectral domain Doppler OCT.

This OCT system 100 is only an example of one OCT imaging modality which can be used to image blood flow with a temporally oscillating magnetic field, and is not intended to suggest any limitation on the scope of OCT architectures applicable to the embodiments disclosed herein. Generally, the OCT system 100 includes a general-purpose computing device in the form of a computer 101 and includes a magnet control 114 and a magnet 116.

Light energy is generated by a light source 117. The light source 117 can be a broadband laser light source coupled into optical fiber emitting light energy over a broad range of optical frequencies. The wavelength range can be from about 400 nanometers to about 1400 nanometers. Longer wavelengths (>600 nm) can be used for deeper scanning Preferably, the light source emits light having a wavelength near the infrared spectrum to identify hemoglobin for OCT imaging, which places hemoglobin in motion and increases optical scattering of the hemoglobin. The light energy can be emitted over a multiplicity of optical wavelengths, frequencies, and pulse durations to achieve OCT imaging. As used herein, optical fiber can refer to glass or plastic wire or fiber. Optical fiber is indicated on FIG. 6 as lines connecting the various blocks of the figures. Where light energy is described as "passing," "traveling," "returning," "directed," or similar movement, such movement can be via optical fiber.

A fraction of the generated light energy passes from the light source 117 into an optical spectrum analyzer 118. The optical spectrum analyzer 118 measures optical frequency as the light energy is emitted from the light source 117 as a function of time. The optical spectrum analyzer 118 samples a portion of the light emitted by the light source 117. The optical spectrum analyzer 118 monitors the power spectral density of light entering the splitter 119. The remaining fraction of light energy from the light source 117 passes into a splitter 119. The splitter 119 can be a device with four ports, with Port 1 allowing light energy to enter the splitter 119. Ports 2 and 3 allow light energy to leave and re-enter the splitter 119 to the reference reflector 120 and OCT probe 122, respectively. Port 4 allows light energy to leave the splitter 119 to coupling lens 124. The splitter 119 couples the light into Port 1. The splitter 119 divides the light according to a pre-determined split ratio selected by a user. For example, the split ratio can be 50/50 wherein half of the light energy entering the splitter 119 at Port 1 exits the splitter 119 through Port 2 and half exits the splitter 119 through Port 3. In another example, the split ratio can be 60/40 wherein 60% of the light energy passes through Port 2 and 40% of the light energy passes through Port 3.

A fraction of the light energy (determined by the split ratio) that exits the splitter 119 through Port 2 travels to a reference reflector surface 120. The light energy is reflected from the reference reflector surface 120 back to the splitter 119 into Port 2. The reference reflector 120 can be a planar metallic mirror or a multilayer dielectric reflector with a specified spectral amplitude/phase reflectivity. The remaining fraction of light that entered splitter 119 through Port 1 exits splitter 119 through Port 3 and enters an OCT probe 122. The OCT probe 122 can be a turbine-type catheter as described in Patent Cooperation Treaty application PCT/US04/12773 filed Apr. 23, 2004 which claims priority to U.S. provisional application 60/466,215 filed Apr. 28, 2003, each herein incorporated by reference for the methods, apparatuses and systems taught therein. The OCT probe 122 can be located within a subject 121 to allow light reflection off of subject's 121 blood flow.

The light energy that entered OCT probe 122 is reflected off of the blood flow of subject 121. once an oscillating magnetic field has been temporally applied by magnet 116. The reflected light energy passes back through the OCT probe 122 into the splitter 119 via Port 3. The reflected light energy that is returned into Port 2 and Port 3 of the splitter 119 recombines and interferes according to a split ratio. The light recombines either constructively or destructively, depending on the difference of pathlengths. A series of constructive and destructive combinations of reflected light create an interferogram (a plot of detector response as a function of optical path length difference). Each reflecting layer from the subject 121 and the blood flow will generate an interferogram. The splitter 119 can recombine light energy that is returned through Port 2 and Port 3 so that the light energies interfere. The light energy is recombined in the reverse of the split ratio. For example, if a 60/40 split ratio, only 40% of the light energy returned through Port 2 and 60% of the light energy returned through Port 3 would be recombined. The recombined reflected light energy is directed out Port 4 of the splitter 119 into a coupling lens 137. The coupling lens 137 receives light from the output of the splitter 119 and sets the beam etendue (beam diameter and divergence) to match that of the optical spectrometer 138. The coupling lens 137 couples the light into an optical spectrometer 138. The optical spectrometer 138 can divide the recombined reflected light energy light into different optical frequencies and direct them to different points in space which are detected by a line scan camera 139. The line scan camera 139 performs light to electrical transduction resulting in digital light signal data 108. The digital light signal data 108 is transferred into the computer 101 via the OCT input interface 111. Interface between the line scan camera 139 and computer 101 can be a Universal Serial Bus (USB), or the like. The digital light signal data 108 can be stored in the mass storage device 104 or system memory 112 and utilized by the image construction software 106 and the Labview image construction software 107.

The image construction software 106 can generate an image of the blood flow of subject 121 from the light signal data 108, by receiving light signal data 108 generating amplitude and phase data. The amplitude and phase data (optical path length difference ($c\tau$) or optical time-delay ($\tau$)) can be separated into discrete channels and a plot of intensity vs. depth (or amplitude vs. depth) can be generated for each channel. Such plot is known as an A-scan, where the composition of all the A-scans can comprise one image. And movement image construction software 107 generates an image of the movement of the hemoglobin from the light signal data 108. The movement image construction software 107 receives light signal data 108 for at least two successive sweeps of the light source 117 or the light source performs a Fourier transform on the light signal data 108 generating amplitude and phase data.

Figure 7:
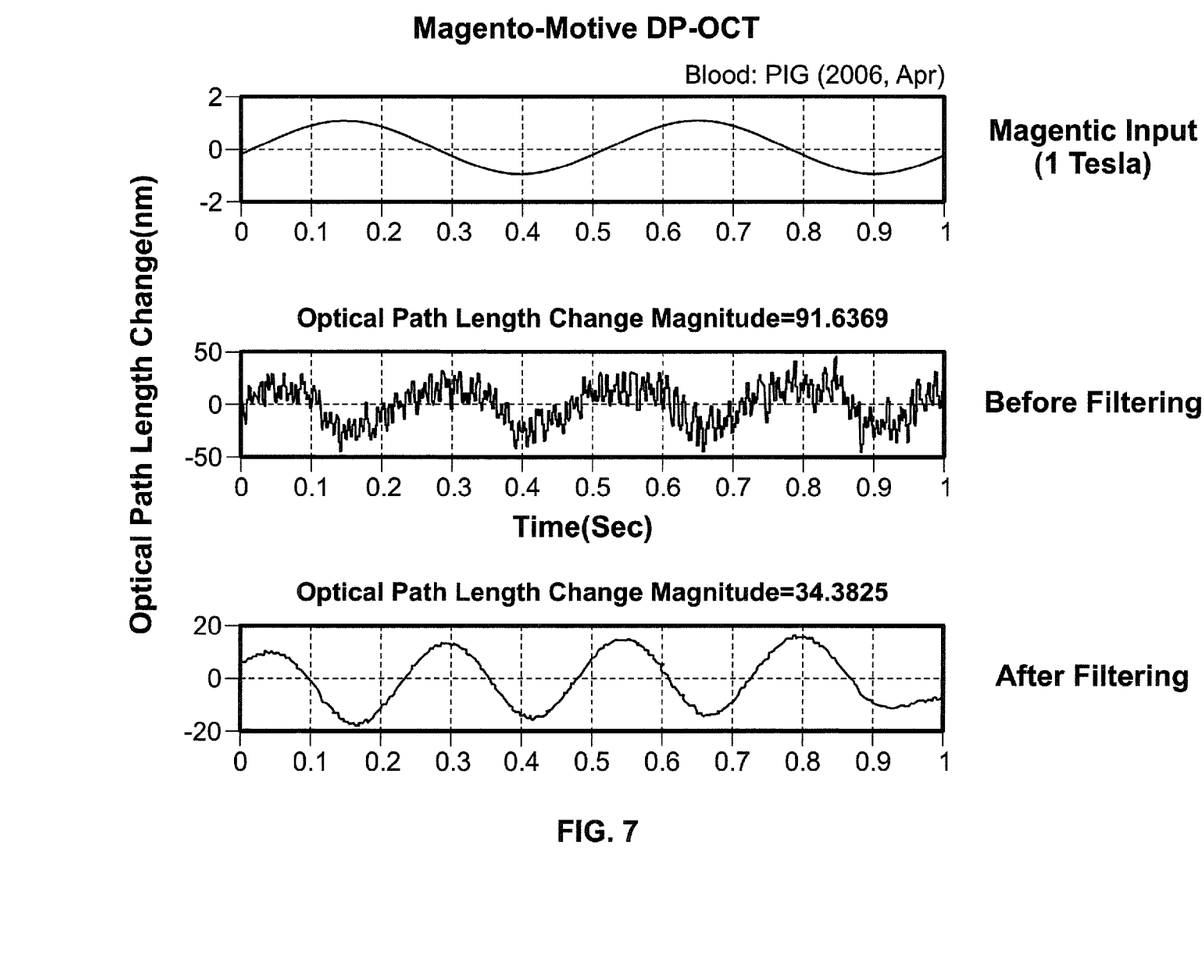
FIG. 7 is a graph of the optical path length change in the DP-OCT system.

Optionally, additional information can be extracted from the light signal data to generate additional images. The light signal data can be further processed to generate a Stokes parameter polarimetric image when used in conjunction with polarization detectors and polarizing lenses to extract polarization data from the light signal 108, as readily known to one skilled in the art of optical coherence tomography. The differential phase OCT image data is shown in FIG. 7, indicating the optical path difference with the magnetic field. Filters can be added to reduce the noise of the signal generated by the magnetic field.

Alternatively, the phase sensitive OCT system 100 can be configured for swept source OCT, which is a different type of spectral domain OCT. In swept source OCT, a tunable laser source replaces the broadband laser light source 117. The scanning rate can be at wavelengths of 800 nm-1500 nm. Also, the reference reflector surface 120 is in-line with sample path 120. The optical spectrometer 125 and line scan camera 126 are replaced with a general photodetector.

The OCT system coupled with an oscillating magnetic field could be used for diagnostic purposes, as detailed above with the MM-ODT system. Since the resolution of OCT is on the order of 2-3 mm into the tissue of a patient, OCT coupled with a magnetic field could image increased blood vessel formation of superficial cancers, such as skin, lung, colon, esophageal, stomach, and the like at an earlier stage. By comparing the concentration of deoxygenated hemoglobin compared to normal tissues, superficial cancers can be diagnosed accordingly. Such a diagnosis could be performed by imaging regions of where superficial cancers occur, imaging such a region with an oscillating magnetic field and an OCT system probe, in order to detect areas with abnormal blood vessel growth which would be indicative of angiogenesis. Alternatively, when imaging the prostate with OCT and an oscillating magnetic field, comparing the OCT image to what a normal OCT image looks like; diagnosis is possible if increase blood vessel formation appears. Optical coherence tomography and Doppler OCT can be used to diagnosis superficial cancers when coupled with an oscillating magnetic field.

In another embodiment, an enhanced detection of cancer with ultrasound imaging 200 is provided. Ultrasonography is the ultrasound-based diagnostic imaging technique used to visualize muscles and internal organs, their size, structures and any pathological lesions. "Ultrasound" applies to all acoustic energy with a frequency above human hearing (20,000 Hertz or 20 kilohertz). Typical diagnostic sonography scanners operate in the frequency range of 2 to 13 megahertz, hundreds of times greater than this limit. The choice of frequency is a trade-off between the image spatial resolution and penetration depth into the patient, with lower frequencies giving less resolution and greater imaging depth. Doppler ultrasonography uses the Doppler Effect to assess whether blood is moving towards or away from a probe, and its relative velocity. By calculating the frequency shift ($v_D$) of a particular sample volume, for example a jet of blood flow over a heart valve, its speed and direction can be determined and visualized. Ultrasonagraphy and Doppler Ultrasonagraphy can best be understood by S. A. Kana *Introduction to physics in modern medicine*, Taylor & Francis, (2003). The basic physics of the Doppler Effect involving acoustic and electromagnetic waves of OCT is similar and many of the signal processing techniques (hardware and software) used to estimate the Doppler shift is analogous.

Figure 8:
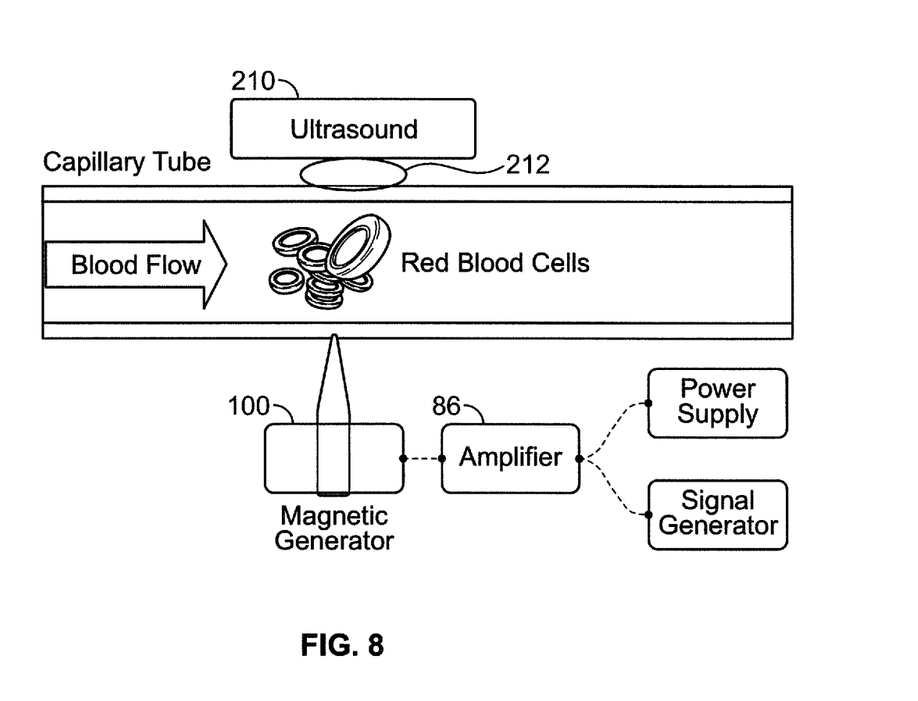
FIG. 8 is a schematic diagram of Magneto Motive Ultrasound for Blood.

In one embodiment, an ultrasound probe 212 is coupled with the magnetic field generator 100, as shown in FIG. 8. Ultrasound 210 is directed into the body of the patient by known techniques when coupled to a probe. Moving red blood cells backscatter the ultrasonic energy back towards the transducer of the ultrasound. The oscillating magnetic field generated by the magnetic field generator 100 increases the contrast of the ultrasonic energy 210 received from the red blood cells. The transducer then converts the back-scattered ultrasonic energy 210 into an electrical signal that is processed in some known manner to determine an estimate of the flow and determine an ultrasound image. An enhanced ultrasound image is produced, as displayed in FIG. 9.

Figure 9:
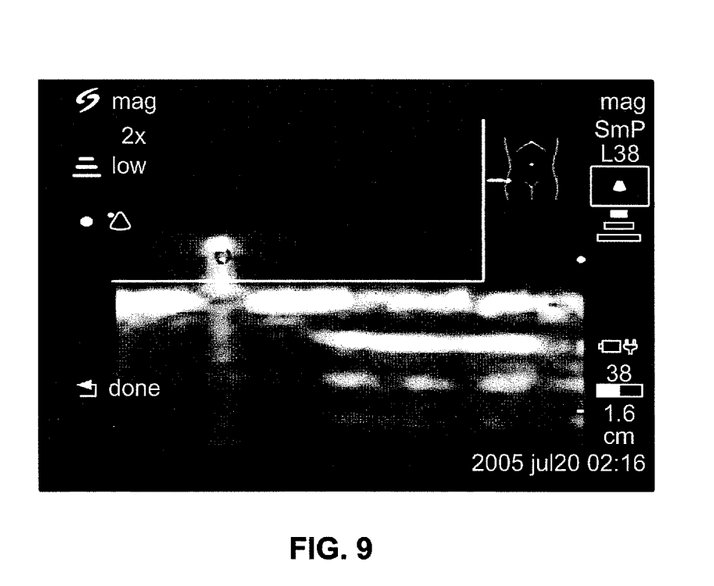
FIG. 9 is an ultrasound image of blood exposed to an oscillating magnetic field.

In one example, a rectal ultrasound probe is coupled with a magnet field generator to evaluate the prostate gland for cancer. Currently, ultrasound is used for prostate cancer screening; however, the approach provides poor sensitivity and specificity. Yet, all cancers are known in the art to be highly vascular due to angiogenesis. Angiogenesis is a process of new blood vessel growth from preexisting blood vessels. Angiogenesis is a fundamental step of tumors from a dormant state to a malignant state, with new blood vessels penetrating into cancerous growths and supplying nutrients and oxygen. Since blood vessels carry hemoglobin, a magnetic field generator 100 is able to provide a magneto-motive force due to the hemoglobin magnet volume susceptibility. When the oscillating magnetic field is coupled with ultrasound detection system, the contrast available from the endogenous RBC's is enhanced in the prostate for cancer detection at an earlier stage. It is generally known in the art that cancers have enhanced metabolic properties compared to normal tissues, so then cancerous cells have higher oxygen content from hemoglobin and a greater concentration of deoxygenated hemoglobin compared to normal tissues. Alternatively, when imaging the prostate with ultrasound and an oscillating magnetic field, comparing the ultrasound image to what a normal ultrasound image looks like; diagnosis is possible if increase blood vessel formation appears in the ultrasound image. Abnormal blood vessel formation could also be indicative of diseased tissue. For example, abnormal vascular patterns could be indicative of angiogenesis and putative prostate cancer. Abnormal vascular patterns would be any vascular patterns outside the normal vasculature anatomy of the prostate. An exemplary ultrasound image for prostate cancer screening is shown in FIG. 9. Both Ultrasonography and Doppler Ultrasonography can be used for diagnosis of prostate cancer when coupled with an oscillating magnetic field.

Another example of cancer diagnosis would include breast cancer. An ultrasound is typically used to determine if a mammogram indicates a solid mass inside the breast region; however, an ultrasound cannot determine if a solid mass is cancerous. However, when an ultrasound probe is coupled with a magnetic field generator 100, the magnetic field generator is able to provide a magnetic field gradient to provide a torque on hemoglobin molecules, i.e. hemoglobin's magnetic volume susceptibility. Hemoglobin molecules which have increased due to angiogenesis, thus provides an enhanced contrast with the magnetic field gradient and ultrasound. The cancerous cells in the breast with the higher oxygen content from hemoglobin and a greater concentration of deoxygenated hemoglobin could be imagined and diagnosed accordingly, when compared to normal breast tissue. Alternatively, when imaging the breast with ultrasound and an oscillating magnetic field, comparing the ultrasound image to what a normal ultrasound image looks like; diagnosis is possible if increased or abnormal blood vessel formation appears.

Alternative examples of diagnostic techniques include any diseased tissue with increased blood vessel formation, which could be detectable by an OCT or ultrasound probe coupled with a magnetic field generator. Angiogenesis is known to occur during coronary artery disease, peripheral artery disease, and stroke when there's insufficient blood supply. For example are the blood vessels that surround large arteries or perfuse large arterial walls, such as vaso vasorum. These vessels surround the artery around the heart. If there is a plaque in these blood vessels, then the blood supply grows as the plaque size increases, and more cells from these additional blood vessels move into the plaque, making it unstable and more likely to rupture causing heart attacks and strokes. It has been shown that the endothelium of the vaso vasorum is disturbed in hypercholesterolemic conditions. This induces constriction of the vaso vasorun with subsequent lack of oxygen supply. Subsequently VEGF expression will increase with rapid vaso vasorum vessel formation as a consequence. Such increased blood vessel formation could be detectable by above described systems, as to diagnose susceptible myocardial infarction or ischemic conditions.

"Diseased tissue" any tissue which is abnormal condition of the body. Cancers detectable by OCT or ultrasound include, but not limited to, squamous cell carcinoma, fibrosarcoma, sarcoid carcinoma, melanoma, mammary cancer, lung cancer, colorectal cancer, renal cancer, osteosarcoma, cutaneous melanoma, basal cell carcinoma, pancreatic cancer, bladder cancer, liver cancer, brain cancer, ovarian cancer, prostate cancer, leukemia, melanoma, or lymphoma Alternatively, diseased tissue with a decrease blood vessel formation may be diagnosed with an OCT or ultrasound probe coupled with a magnetic field generator. Such examples include blood vessel formation associated with arteriosclerosis, myocardial infarction, and ischemia. In these examples, the normal blood vessel image is compared to a diseased state image, and diagnosed when the normal blood vessel formation is cut off or decreased due to ischemic conditions.

Figure 10:
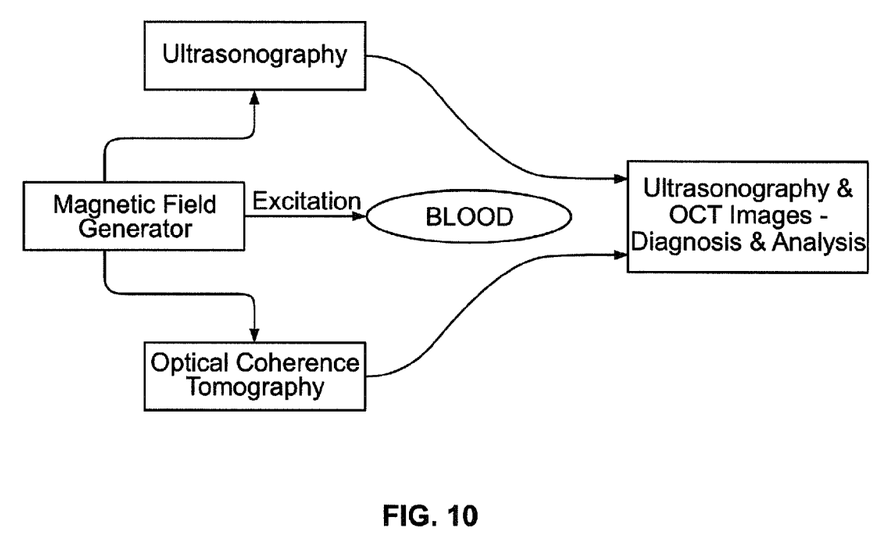
FIG. 10 is a schematic diagram of Ultrasonography and OCT coupled with magnetic field generator.

MM-ODT, OCT, and ultrasound coupled with an oscillating magnetic field all can be used in clinical management of patients who need microvasculature monitoring, as shown in FIG. 10. The images could monitor and determine tissue profusion and viability before, during and after operation procedures. For example, the images could be used to detect oxygenated and deoxygenated blood supply, detect blood vessel location, sizes of cancer, vascular tissue abnormality identification, and port-wine stain. Alternatively, the images could monitor photodynamic therapy or evaluate cranial injuries. While medical applications of the embodiments disclosed herein have been described, the embodiments are applicable to any circumstance where image contrast is needed for fluids comprising endogenous metallic compositions. MM-ODT, OCT, and ultrasound can be used in various combinations to detect vascular occurrences.

While the invention has been described in connection with various embodiments, it will be understood that the invention is capable of further modifications. This application is intended to cover any variations, uses or adaptations of the invention following, in general, the principles of the invention, and including such departures from the present disclosure as, within the known and customary practice within the art to which the invention pertains.

What is claimed is:

1. A system for diagnosing diseased tissue, comprising:
   a. a detection system coupled to a probe for transmitting and receiving energy to and from a subject; and
   b. a magnetic field generator coupled to the probe, wherein the magnetic field generator generates an oscillating magnetic field including includes a strength and oscillation sufficient to induce a detectable magnetic movement of a blood flow or a blood supply having a magnetic susceptibility of about $11 \times 10^{-6}$ and wherein the detection system is operable to detect the displacement of the blood supply or blood flow affected by the oscillating magnetic field.

2. The system of claim 1, wherein the detection system is an ultrasound detection system.

3. The system of claim 2, wherein the ultrasound detection system is a Doppler ultrasound detection system.

4. The system of claim 1, wherein the detection system is an optical coherence tomography system.

5. The system of claim 4, wherein the optical coherence tomography system is a Doppler optical coherence tomography system.

6. The system of claim 1, wherein the oscillating magnetic field includes a strength and oscillation rate greater than or equal to 50 Hz sufficient to induce a detectable magnetic movement of a blood flow or a blood supply.

7. The system of claim 1, wherein the magnetic field is oscillating and being greater than or equal to 0.14 T at a time during each oscillatory cycle.

8. The system of claim 1, wherein the detection system is an optical coherence tomography system that compares the image of the blood flow or the blood supply of the suspected diseased tissue to an image of a blood flow or a blood supply from a normal tissue.

9. The system of claim 1, wherein the optical coherence tomography system is a Doppler optical coherence tomography system for detecting the blood flow affected by the magnetic field of an at least 100 Hz Doppler frequency shift.

10. A system for diagnosing diseased tissue, comprising:
   a. a detection system coupled to a probe for transmitting and receiving energy to and from a subject; and
   b. a magnetic field generator coupled to the probe, wherein the magnetic field generator generates an oscillating magnetic field being greater than or equal to 0.14 T at a time during each oscillatory cycle and wherein the detection system is operable to detect the displacement of the blood supply or blood flow affected by the oscillating magnetic field.

11. The system of claim 10, wherein the detection system is an ultrasound detection system that compares the image of the blood flow or the blood supply of the suspected diseased tissue to an image of a blood flow or a blood supply from a normal tissue.

12. The system of claim 11, wherein the ultrasound detection system is a Doppler ultrasound detection system.

13. The system of claim 10, wherein the detection system is an optical coherence tomography system that compares the image of the blood flow or the blood supply of the suspected diseased tissue to an image of a blood flow or a blood supply from a normal tissue.

14. The system of claim 13, wherein the optical coherence tomography system is a Doppler optical coherence tomography system.

* * * * *